United States Patent [19]

Li

[11] Patent Number: 4,828,823

[45] Date of Patent: May 9, 1989

[54] DICALCIUM PHOSPHATE DIHYDRATE FOR FLUORIDE DENTIFRICE COMPOSITIONS

[75] Inventor: Rosa Li, Vernon, Conn.

[73] Assignee: Stauffer Chemical Company, Shelton, Conn.

[21] Appl. No.: 848,861

[22] Filed: Apr. 7, 1986

[51] Int. Cl.$^4$ .......................... A61K 7/18; A61K 7/16
[52] U.S. Cl. ......................................... 424/52; 424/57; 423/267; 423/308; 423/309
[58] Field of Search .................... 424/52, 57; 423/267, 423/308–309

[56] References Cited

U.S. PATENT DOCUMENTS

| | | | |
|---|---|---|---|
| 4,244,931 | 1/1981 | Jarvis et al. | 424/57 |
| 4,312,843 | 1/1982 | Monty et al. | 424/57 |
| 4,472,365 | 9/1984 | Michel | 423/267 |

*Primary Examiner*—Howard E. Schain
*Assistant Examiner*—F. T. Moezie
*Attorney, Agent, or Firm*—Paul J. Juettner

[57] ABSTRACT

The monofluorophosphate compatibility of dicalcium phosphate dihydrate can be improved in processes in which a slaked lime slurry is reacted with phosphoric acid to form a monocalcium phosphate solution to which is added magnesium oxide, additional lime slurry and pyrophosphoric acid with later removal of the dicalcium phosphate dihydrate. The improvement involved adding the magnesium oxide at 0.3%–2% and adding 0.1%—less than 0.5% of trimagnesium phosphate to the recovered dicalcium phosphate dihydrate.

9 Claims, No Drawings

DICALCIUM PHOSPHATE DIHYDRATE FOR FLUORIDE DENTIFRICE COMPOSITIONS

BACKGROUND (i) Field of the Invention

This invention relates generally to improved dentifrice compositions. More particularly, it relates to toothpaste and related products prepared from both a source of fluoride ions (such as sodium monofluorophosphate) and dicalcium phosphate dihydrate (as a dental polishing agent). Even more particularly, it relates to the avoidance of the use of an excessive amount of trimagnesium phosphate and its hydrates in such toothpaste compositions.

(ii) Related Prior Art

Many dentifrice compositions, e.g., toothpastes, today comprise four or more ingredients essential for effectiveness: (1) a water-soluble fluoride compound (such as sodium monofluorophosphate) as an anti-cariogenic agent; (2) a dispersant comprising water; (3) dicalcium phosphate dihydrate (hereinafter DCPD) as a polishing agent; (4) humectant, such as glycerine or sorbitol; (5) one or a group of several optional stabilizers intended to maintain the essential properties of the toothpaste during storage over a period of possibly years; and (6) optional surfactants.

A long-addressed problem with such prior art toothpastes is their tendency to "age" in several different ways. Firstly, the monofluorophosphate ingredient is converted from a water-soluble form to an insoluble form, apparently by reaction with the dicalcium phosphate dihydrate. This reduces the concentration of the fluoride ions. Secondly, some stabilizers that reduce the reactivity of the dicalcium phosphate dihydrate (thereby preventing it from "setting up" and the toothpaste becoming lumpy), themselves convert the monofluorophosphate into an insoluble form. The foregoing problem has been defined as "monofluorophosphate (or MFP) incompatibility of the DCPD". The problem is further compounded by the fact that the dicalcium phosphate dihydrate raw material itself has to be stabilized against degradation during manufacture and storage prior to use, in a different and non-toothpaste environment.

Prior art relating to the use of a magnesium phosphate as an ingredient in a composition comprising dicalcium phosphate dihydrate includes the following: U.S. Pat. Nos. 4,472,365 (Michel); 4,312,843 (Monty et al.); 4,487,749 (Sherif et al.); 4,496,527 (Sherif et al.); 4,016,255 (Forward et al.); 3,411,876 (Harnisch et al.); and 3,294,786 (Cremer et al.); British Pat. No. 1,548,465 (assigned to Hoechst AG); and the abstract of Japanese Pat. No. 58,052,209-A (assigned to Lion Corp.). Essentially, none of the foregoing discloses the invention claimed hereinafter wherein dicalcium phosphate dihydrate compositions (and toothpastes prepared therefrom) comprise trimagnesium phosphate octahydrate in a critically small range.

Stauffer Chemical Company's U.S. Pat. No. 4,472,365 (Michel) is of particular interest and is hereby incorporated by reference. Michel's invention is mainly directed to the addition of relatively small amounts of magnesium oxide to the reaction mixture during the preparation of dicalcium phosphate dihydrate, in order to improve the "monofluorophosphate compatibility" of the final product. In a preferred embodiment of Michel's invention, dimagnesium phosphate, trimagnesium phosphate or mixtures thereof are optionally blended with the dicalcium phosphate dihydrate in an amount from about 0.5% to about 5% by weight of the dicalcium phosphate dihydrate (see col. 5, lines 22 to 43 and claim 3). They are merely described as being effective to reduce "caking" or "lumping" of the dicalcium phosphate dihydrate and are not described as exerting any effect on the fluoride compatibility of a dicalcium phosphate dihydrate-containing toothpaste in which they might also be present.

There has also been commercial use, for more than one year, of some embodiments of the subject matter of the foregoing Michel patent, with trimagnesium phosphate octahydrate incorporated at the 0.8–1.35 weight percent level.

Stauffer Chemical Company's U.S. Pat. No. 4,312,843 (Monty et al.) relates to dicalcium phosphate dihydrate compositions having improved monofluorophosphate compatibility that are prepared by adding pyrophosphoric acid to the dicalcium phosphate reactor; terminating the reaction by which the dicalcium phosphate is formed at a pH ranging from 4.9 to 5.5; and blending the final product with a stabilizing agent. Monty also discloses that trimagnesium phosphate octahydrate and dimagnesium phosphate trihydrate are both effective as stabilizing agents as judged by monofluorophosphate compatibility. Dimagnesium phosphate was particularly effective, in this regard, at concentrations in the range of from 1 to 5% by weight as giving better fluoride compatibility readings than trimagnesium phosphate.

British Pat. No. 1,548,465 assigned to Hoechst AG relates to the precipitation of dimagnesium phosphate trihydrate either onto or jointly with the precipitation of dicalcium phosphate dihydrate. The product comprises 1–50 (preferably 2–20) weight percent of dimagnesium phosphate trihydrate, based on the dicalcium phosphate dihydrate. The effect of trimagnesium phosphate is not touched upon by this reference.

SUMMARY OF THE INVENTION

In contrast to the aforementioned prior art, it has now been found that the amount of trimagnesium phosphate octahydrate is important since excess material causes a decrease in total soluble fluoride results. It has also been found that less than 0.5 weight percent, e.g. about 0.25–0.40 weight percent, of trimagnesium phosphate octahydrate is sufficient to provide dry stability of the dicalcium phosphate dihydrate without significant loss of monofluorophosphate compatibility.

DETAILED DESCRIPTION OF THE PRESENT APPLICATION

The present invention relates to a process for forming dicalcium phosphate dihydrate having improved monofluorophosphate compatibility. The process of the present invention is an improvement of the process described in U.S. Pat. No. 4,472,365 to C. G. Michel, which is incorporated herein by reference.

The Michel process forms dicalcium phosphate dihydrate by the following process.

(1) reaction of a slaked limed slurry with phosphoric acid to form a monocalcium phosphate solution. The slaked lime slurry is prepared by mixing lime with either water, or recycled mother liquor remaining after removal of the dicalcium phosphate dihydrate from the final slurry, or both. The acid used is preferably a food grade acid. The compositional range for the monocalcium phosphate solution will be approximately: 2-4 wt % CaO; 12-22 wt % $P_2O_5$; and 1-2 pH value.

(2) adding magnesium oxide to the monocalcium phosphate solution with additional slaked lime slurry. This MgO addition is conducted preferably when the pH is in the range of from about 1 to about 4. In accordance with the present invention, the amount of magnesium oxide added is controlled to achieve the desired improvement. The additional slaked lime slurry is also added. The net result is the formation of a dicalcium phosphate dihydrate slurry having a pH of from 5.4 to about 5.9.

(3) adding into the dicalcium phosphate dihydrate slurry an amount of pyrophosphoric acid sufficient to reduce the pH to from about 4.9 to about 5.5. The amount of pyrophosphoric acid should be from 0.1%-1.0% by weight of the dicalcium phosphate dihydrate to be produced.

(4) separating the dicalcium phosphate dihydrate from the slurry.

In accordance with the present invention, the monofluorophosphate compatibility of the decalcium phosphate dihydrate produced by the above type process is improved if:

(a) the amount of magnesium oxide added in Step (2) is at least 0.3% by weight of the calcium oxide content of the slurry, preferably about 0.5-2.5%, most preferably 0.7-1.4%; and (b) if the dicalcium phosphate dihydrate product is blended with less than 0.5% of its weight with trimagnesium phosphate, preferably 0.1-0.4%, most preferably 0.2-0.3%.

The dicalcium phosphate dihydrate product of this invention is a suitable polishing agent for dentifrices as will now be described.

The type of fluoride dentifrice to which the present invention relates is well known. A representative patent describing such dentifrice formulations is U.S. Pat. No. 4,348,382 to Pierce et al.

The fluoride source is sodium monofluorophosphate which is present at from about 0.05 to about 7.5% by weight of the composition, generally from about 0.05-1%. It can optionally be mixed with an additional, lesser amount of fluoride source (e.g., sodium fluoride, potassium fluoride, or stannous fluoride) in a weight ratio of about 9:1 to 3:2.

The polishing agent is predominantly finely divided dicalcium phosphate dihydrate. It is preferably finely divided, e.g., having an average particle size below about 45 microns. It is possible to mix the DCPD with a minor amount of one or more additional dentally acceptable polishing agents which do not substantially adversely affect fluoride retention or compatibility. Included are anhydrous dicalcium phosphate, calcium carbonate, silica, calcined alumina, hydrated alumina, calcium pyrophosphate, tricalcium phosphate, and calcium metaphosphate. The amount of DCPD is about 65% or greater of the total weight of the polishing agent. The polishing agent is generally 20-75% by weight of the dentifrice.

Surface active and detersive materials are preferably included in the dentifrice at from about 0.5% to about 5% by weight of the dentifrice. Examples include the water soluble salts of higher fatty acid monoglyceride monosulfate detergents, the higher alkyl sulfates (e.g., sodium lauryl sulfate), the higher fatty acid esters of 1,2-dihydroxy propane sulfonate, and the like.

The dentifrice can be in solid, liquid or paste form. Generally the liquids used in cream or paste forms will comprise water, glycerine, sorbitol, propylene glycol, or the like, including appropriate mixtures thereof. Mixtures of water with a humectant or binder or glycerine, sorbitol or mixtures thereof are preferred. The total liquid content will generally be 20-75% of the dentifrice. Gums (e.g., Irish Moss, gum tragacanth, sodium carboxymethyl cellulose, polyvinylpyrollidone, starch, and the like) can also be used at 0.5-5% by weight of the dentifrice.

Optional adjuvants such as coloring or whitening agents, preservatives, silicones, chlorophyll compounds, antibacterial agents, and flavoring materials may be used in conventional amount.

EXAMPLE 1

Samples of dicalcium phosphate dihydrate were prepared according to general procedures described in aforementioned Michel's U.S. Pat. No. 4,472,365. In particular, the process involved the following four steps: (1) reacting a slaked lime slurry with phosphoric acid to form a monocalcium phosphate solution; (2) adding magnesium oxide (in the form of $Mg(OH)_2$) into the solution and adding additional slaked lime slurry in an amount sufficient to form a dicalcium phosphate dihydrate slurry having a pH ranging from about 5.4 to about 5.9; (3) adding into the dicalcium phosphate dihydrate slurry an amount of pyrophosphoric acid sufficient to reduce the pH of the slurry to from about 4.9 to about 5.5, provided, however, that the minimum amount of pyrophosphoric acid so added was at least 0.1% by weight of dicalcium phosphate dihydrate; and (4) separating the dicalcium phosphate dihydrate from the slurry in a conventional manner.

More specifically, magnesium oxide was added in step (2) in the form of magnesium hydroxide and in an amount of about 0.97 weight percent of magnesium oxide based on the weight of feedstock calcium oxide. Also, pyrophosphoric acid was added in step (3) in an amount of from about 0.2-0.4% by weight of dicalcium phosphate dihydrate.

The foregoing going separated dicalcium phosphate dihydrate was then subjected to the following further steps: (5) dried; (6) ground into particles having an average particle diameter within the range of about 5-6 microns (with at least 99% by weight of the particles being capable of passing through a U.S. Standard Sieve No. 325); and (7) intimately blended with trimagnesium phosphate octahydrate in amounts of 0, 0.25, 0.50, 0.75 and 1.50 weight percent, based on the weight of dicalcium phosphate dihydrate and additive. The foregoing was essentially repeated on five DCPD samples (except at the 1.50% level, which was repeated on only one additional sample). Accordingly, 22 samples were prepared.

A first part of each of these 22 samples was then evaluated for "Dry Stability". The dry stability test subjects a 3 gm. sample of DCPD to a temperature of 800° C. until a constant weight is recorded. The calculated percent DCPA (dicalcium phosphate, anhydrous) content is then derived through calculation. The theoretical calculated value is about 26.2% LOI. The LOI is determined the same way on a sample that was aged for 48 hours at 60° C. in 75% relative humidity. The greater the drop in LOI value and the greater the increase in calculated percent DCPA, the more prone the DCPD sample is to loss of water by hydration with conversion to the DCPA form. The calculated values of percent dicalcium phosphate, anhydrous (DCPA) for each of the DCPD samples are shown in Table 1A below.

TABLE 1A

| Wt. % of TMP | % DCPA | | | | |
|---|---|---|---|---|---|
| | Sample 1 | Sample 2 | Sample 3 | Sample 4 | Sample 5 |
| 0. | 0.62 | 5.0 | 4.03 | 3.7 | 0.5 |
| 0.25 | 1.40 | 0. | 0.8 | 0. | 0. |
| 0.50 | 2.48 | 0. | 0.8 | 0.8 | 0. |
| 0.75 | 0.20 | 0. | 0. | 0. | 0. |
| 1.50 | — | 0. | — | 0. | — |

It was concluded from Table 1A that very small quantities of TMP (around 0.25 weight percent) were fully adequate to provide dry stability on a production basis wherein the upper control limit is set at 8% DCPA.

A second portion of each of the foregoing 22 samples was used to prepare 22 different toothpastes (having the type of formulation described hereinbefore). Each of the 22 toothpastes was evaluated for monofluorophosphate compatibility by the aforedefined accelerated test at 49° C. for 3 weeks. In addition the pH of each toothpaste was measured at the beginning and end of each fluoride compatibility test. In general, the pH of the toothpaste fell about 1±0.3 (e.g. from 7.6 to 6.6). The initial fluoride levels were determined before the aging; the final, after aging. The results of the compatibility test are shown in Table 1B below which give the parts per million of soluble fluoride.

TABLE 1B

| | TOTAL SOLUBLE FLUORIDE (F⁻ ppm) | | | | |
|---|---|---|---|---|---|
| Wt. % of TMP | Sample 1 Initial/ Final | Sample 2 Initial/ Final | Sample 3 Initial/ Final | Sample 4 Initial/ Final | Sample 5 Initial/ Final |
| 0. | 960 700 | 1010 710 | 970 780 | 1060 790 | 980 730 |
| 0.25 | 950 700 | 1030 700 | 980 730 | 1050 760 | 950 710 |
| 0.50 | 970 690 | 1030 690 | 980 740 | 1040 750 | 1000 710 |
| 0.75 | 970 660 | 1010 650 | 970 730 | 1010 730 | 980 700 |
| 1.50 | — — | 1030 620 | — — | 1010 680 | — — |

These data show that with increasing TMP content, especially at above 0.50% TMP, the fluoride compatibility generally decreases after aging. The approximate potential margin of error in the above fluoride analysis is approximately ±30 ppm. In other words, values within this range are considered to be approximately comparable.

EXAMPLE 2

This Example suggests that as little as 0.13 weight percent of TMP is adequate to provide good dry stability, without adversely affecting MFP compatibility of the DCPD. It also confirms the adverse effect of using TMP at a concentration of around 1.5 weight percent.

Example 1 was essentially repeated except for the following: (1) the amount of Mg(OH)₂ added in Step 2 was more than doubled (to 2.14 weight percent of magnesium oxide based on the weight of feedstock calcium oxide); (2) TMP was added at the 0.13 weight percent level instead of the 0.50 weight percent level; and (3) only 1 sample was prepared.

The results of the Dry Stability test are shown in Table 2A below.

TABLE 2A

| | | % DCPA | |
|---|---|---|---|
| | | "Dry" Stability Test | |
| Wt. % of TMP | Initial % LOI | Final % LOI | % DCPA |
| 0 | 26.4 | 24.7 | 7.6 |
| 0.13 | 26.4 | 26.3 | 0 |
| 0.25 | 26.4 | 26.3 | 0 |
| 0.75 | 26.4 | 26.4 | 0 |
| 1.5 | 26.5 | 26.4 | 0 |

The results of the MFP compatibility test are shown in Table 2B below.

TABLE 2B

| | TOTAL SOLUBLE FLUORIDE (F⁻ ppm) | | | |
|---|---|---|---|---|
| Wt. % of TMP | Initial Total Soluble Fluoride | Final Total** Soluble Fluoride | pH before aging | pH after*** aging |
| 0 | 1000 | 760 | 7.5 | 6.4 |
| 0.13 | 990 | 750 | 7.7 | 6.5 |
| 0.25 | 1000 | 740 | 7.9 | 6.5 |
| 0.75 | 980 | 700 | 8.1 | 6.6 |
| 1.5 | 1010 | 660 | 8.2 | 6.9 |

**Ave. values of 2 or 3 tests (F⁻ analysis) on the same paste.
***Ave. values of 2 pH measurements.

As mentioned before in connection with Example 1, the margin for error in the fluoride values is ±30 ppm.

COMPARATIVE EXAMPLE 3

This Comparative Example shows that dry stability and MFP compatibility are not critically dependent upon the amount of dry-blended stabilizer when tetrasodium pyrophosphate (hereinafter TSPP) is used rather than TMP (as in Example 1). However, the dry stability obtained by dry-blending TSPP is inferior to that obtained by using TMP (as in Example 1).

Example 2 was essentially repeated except that tetrasodium pyrophosphate (TSPP) was used in place of TMP, in the amounts as shown in Tables 3A and 3B below, concerning dry stability and MFP compatibility respectively.

TABLE 3A

| | | % DCPA | |
|---|---|---|---|
| | | "Dry" Stability Test | |
| Wt. % of TSPP | Initial % LOI | Final % LOI | % DCPA |
| 0 | 26.4 | 24.7 | 7.6 |
| 0.25 | 26.3 | 25.5 | 3.7 |
| 0.75 | 26.2 | 25.2 | 5.1 |
| 2.0 | 26.0 | 25.4 | 4.2 |
| 3.0 | 25.6 | 25.4 | 4.3 |

TABLE 3B

| | COMPATIBILTIY (F⁻ ppm) | | | |
|---|---|---|---|---|
| Wt. % of TSPP | Initial Total Soluble Fluoride | Final Total** Soluble Fluoride | pH before aging | pH after*** aging |
| 0 | 1010 | 740 | 7.6 | 6.4 |
| 0.25 | 1000 | 760 | 7.8 | 6.5 |
| 0.75 | 1000 | 720 | 7.8 | 6.6 |
| 2.0 | 1000 | 730 | 8.0 | 6.9 |
| 3.0 | 1000 | 730 | 8.2 | 7.1 |

**Ave. values of 2 or 3 tests (F⁻ analysis) on the same paste (or mucilage).
***Ave. values of 2 pH measurements.

EXAMPLE 4

This Example further illustrates the critical effect of the amount of TMP on MFP compatibility when it is used as a dry-blended stabilizer in combination with TSPP.

Example 2 was essentially repeated except that TMP and TSPP were both used with the amounts and test results as shown in Tables 4A and 4B below.

TABLE 4A

| Wt. % of TMP/TSPP | % DCPA | | |
|---|---|---|---|
| | | "Dry" Stability Test | |
| | Initial % L.O.I. | Final % L.O.I. | % DCPA |
| 0 | 26.4 | 24.7 | 7.6 |
| 0.25/2.0 | 26.0 | 25.6 | 3.3 |
| 0.25/0.75 | 26.3 | 25.7 | 2.5 |
| 1.5/2.0 | 26.1 | 25.9 | 1.4 |
| 1.5/0.75 | 26.4 | 26.4 | 0 |

TABLE 4B

| Wt. % of TMP/TSPP | COMPATIBILITY (F$^-$ ppm) | | | |
|---|---|---|---|---|
| | Initial Total Soluble Fluoride | Final Total** Soluble Fluoride | pH before aging | pH after*** aging |
| 0 | 1010 | 750 | 7.5 | 6.5 |
| 0.25/2.0 | 1020 | 730 | 8.2 | 6.7 |
| 0.25/0.75 | 980 | 720 | 7.8 | 6.8 |
| 1.5/2.0 | 1000 | 650 | 8.0 | 7.1 |
| 1.5/0.75 | 970 | 640 | 7.7 | 7.1 |

**Ave. values of 2 or 3 tests (F$^-$ analysis) on the same paste (or same mucilage).
***Ave. values of 2 pH measurements.

What I claim is:

1. An improved process for preparing dicalcium phosphate dihydrate compositions having improved monofluorophosphate compatibility, of the type which comprises the steps of: (a) reacting a slaked lime slurry with phosphoric acid to form a monocalcium phosphate solution; (b) adding to the solution magnesium oxide and additional amounts of lime slurry and from about 0.1% to about 1.0% pyrophosphoric acid, by weight of dicalcium phosphate dihydrate to be formed, to form a dicalcium phosphate dihydrate slurry having a pH ranging from about 4.9 to about 5.5; (c) separating the dicalcium phosphate dihydrate from the slurry; and (d) blending the dicalcium phosphate with a stabilizing agent; wherein the improvement comprises:

the combination of (i) adding magnesium oxide in step (b) in an amount, X%, of at least 0.3% by weight of the calcium oxide; and (ii) adding trimagnesium phosphate in step (d) in an amount, Y%, of less than 0.4 by weight based on the weight of dicalcium phosphate dihydrate.

2. The process of claim 1 wherein X is in the range from 0.5 to 2.

3. The process of claim 2 wherein X is in the range from 0.7 to 1.

4. The process of claim 1 wherein Y is in the range from 0.1 to 0.4.

5. The process of claim 1 wherein Y is in the range from 0.2 to 0.3.

6. The process of claim 1 wherein X is in the range from 0.7 to 1.0 and Y is in the range from 0.2 to 0.3.

7. An improved process for preparing stabilized dicalcium phosphate dihydrate compositions having improved monofluorophosphate compatibility, of the type which comprises the steps of: (a) preparing an aqueous solution comprising calcium ions and phosphate ions; (b) precipitating dicalcium phosphate dihydrate from the solution to form a slurry; (c) precipitating a first stabilizer in the presence of at least some precipitated dicalcium phosphate dihydrate; and (d) blending a second stabilizer with the precipitated dicalcium phosphate dihydrate and the precipitated first stabilizer; wherein the improvement comprises:

the combination of (i) precipitating a first stabilizer comprising dimagnesium phosphate in an amount, X%, of at least 0.15% by weight of calcium oxide in precipitated dicalcium phosphate dihydrate; and (ii) blending a second stabilizer comprising trimagnesium phosphate in an amount, Y%, of less than 0.4% by weight based on the weight of dicalcium phosphate dihydrate.

8. A dicalcium phosphate dihydrate composition resulting from any of the processes of claims 1–7.

9. A fluoride-containing toothpaste which comprises, as a polishing agent, the composition resulting from any of the processes of claims 1–7.

* * * * *